(12) United States Patent
Scott et al.

(10) Patent No.: US 7,482,115 B2
(45) Date of Patent: Jan. 27, 2009

(54) IMMOBILISATION AND STABILISATION OF VIRUS

(75) Inventors: Hugh Scott, Glasgow (GB); Michael Mattey, Cumbernauld (GB)

(73) Assignee: University of Strathclyde (GB)

( * ) Notice: Subject to any disclaimer, the term of this patent is extended or adjusted under 35 U.S.C. 154(b) by 164 days.

(21) Appl. No.: 10/512,635

(22) PCT Filed: Apr. 28, 2003

(86) PCT No.: PCT/GB03/01797

§ 371 (c)(1),
(2), (4) Date: May 31, 2005

(87) PCT Pub. No.: WO03/093462

PCT Pub. Date: Nov. 13, 2003

(65) Prior Publication Data

US 2005/0220770 A1 Oct. 6, 2005

(30) Foreign Application Priority Data

Apr. 27, 2002 (GB) ................. 0209680.8

(51) Int. Cl.
*C12Q 1/70* (2006.01)
*G01N 33/554* (2006.01)
*C12N 7/00* (2006.01)
*C12N 7/06* (2006.01)

(52) U.S. Cl. .................. 435/5; 435/235.1; 435/238; 435/7.32

(58) Field of Classification Search .................. None
See application file for complete search history.

(56) References Cited

U.S. PATENT DOCUMENTS 5,149,653 A * 9/1992 Roser .................. 435/260
5,663,069 A   9/1997 Ray et al.
2002/0001590 A1   1/2002 Kelly et al.
2002/0127547 A1   9/2002 Miller

FOREIGN PATENT DOCUMENTS

DE  198 28 596   2/1999
WO  WO 02/07742   1/2002

OTHER PUBLICATIONS

Bennett, et al. The use of bacteriophage-based systems for the separation and concentration of Salmonella. J Appl Microbiol. 1997; 83:259-265.*
Zhang, et al. J. Polymer Sci. Part A—Polymer Chem. 1995; 33(15):2629-2638.*
Markoishvili, et al. A novel sustained-release matrix based on biodegradable poly(ster amide)s and imprenated with bacteriophages and an antibiotic shows promis in management of infected venous stasis ulcers and other pooly healing wounds. Intl J Dermatol. 2002; 41:452-458.*
International Search Report for PCT/GB2003/001797 completed Oct. 22, 2003.
Marks, T., et al., "Bacteriophages and biotechnology: a review," *Journal of Chemical Technology* and Biotechnology, 2000, pp. 6-17, vol. 75.

* cited by examiner

*Primary Examiner*—Bruce Campell
*Assistant Examiner*—Bo Peng
(74) *Attorney, Agent, or Firm*—Alston & Bird LLP

(57) ABSTRACT

The present invention relates to a method for immobilization and optional stabilization of viruses whilst retaining the viral biological activity and the use of immobilized virus in therapy. In particular, the immobilized virus relates to immobilized bacteriophage and their use as an antibiotic or bacteriostatic agent and in the treatment of antibiotic-resistant infections.

15 Claims, 5 Drawing Sheets

Wound model 1

Wound model 2

IMMOBILISATION AND STABILISATION OF VIRUS

Figure 1:
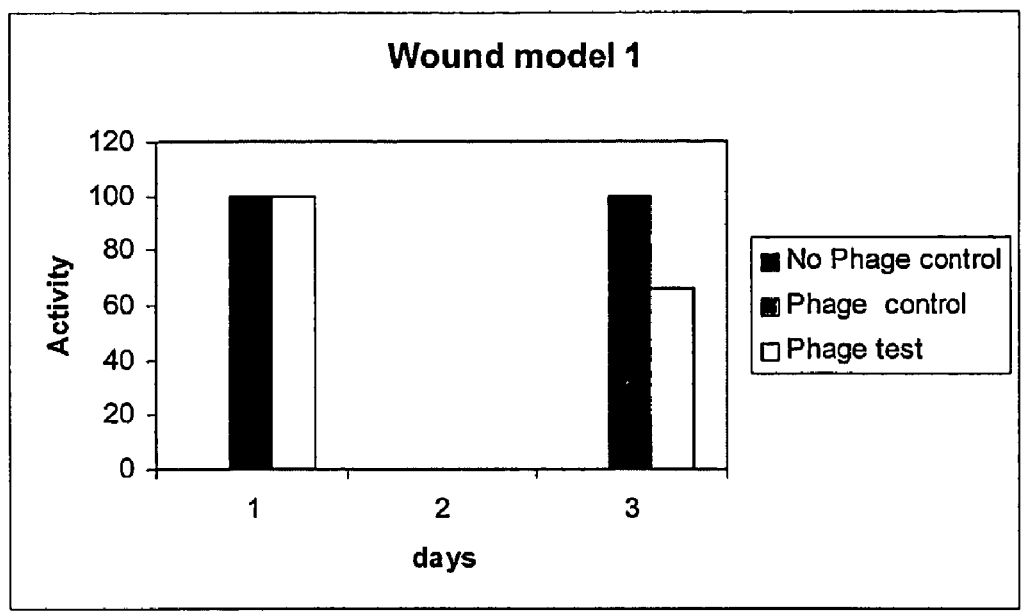

The present invention relates to a method for immobilising and optionally stabilising viruses including bacteriophage, preferably to a solid phase substrate, for use in therapy, in particular as an antibiotic (bactericide) or bacteriostatic agent, in the treatment of antibiotic-resistant superficial infections and use in vaccinations.

Bacteria have proven adept at developing resistance to new anti-microbial agents and so-called "super-bugs" are a cause of rising costs spent on means to combat super-bug-related infections and fatalities in hospitals throughout the world. For example, the use of antibiotics, whether in an individual patient or in a hospital with its special environment and catalogue of micro-organisms, will destroy antibiotic-susceptible bacteria but permit the proliferation of bacteria that are intrinsically resistant or that have acquired extra chromosomal resistance. Thus, the more antibiotics are used, the more resistant bacteria become.

Bacteria can survive on common hospital materials including cotton and/or polyester lab coats, privacy curtains and polyethylene splash aprons for anything up to seven weeks increasing the chance of spreading infection. Indeed, common disinfectants used to sterilise hospital rooms and equipment are not sufficient to curb the spread of "super-bugs".

Furthermore, no fundamentally new antibiotic has been discovered for at least 30 years and there is no guarantee that new classes of antibiotics will be developed let alone even discovered in the next decade.

An alternative to antibiotics in the fight against "super-bugs" is the use of bacteriophage. A bacteriophage is a water-borne virus that infects specific bacteria. Virus particles vary in shape and size, from 0.02 to 0.3 µm and contain RNA or DNA, either double or single stranded, which forms the viral genome. The viruses have a varied structure but the nucleic acid is always located within the virus particle surrounded by a protein coat (capsid or shell). The complex of nucleic acid and protein (the nucleocapsid) may be the whole structure of the virus (for example φ6, an RNA bacterial virus, or φX174, a DNA bacterial virus) but structures that are more complicated occur. The enveloped viruses may have lipid and protein membranes around the capsid while the complex viruses possess not only icosahedral heads but also helical tails with up to 20 proteins within the tail.

Bacteriophage on infection of their hosts can multiply by either a lytic or lysogenic pathway. Bacteriophage that can integrate their DNA into bacterial chromosomes are known as lysogenic bacteriophage, with the integrated viral DNA replicating along with the host chromosome to produce new integrated viral DNA copies. Alternatively, the virus may replicate freely to produce several hundred progeny particles. Lysis of the cells then releases this large number of free viruses, which are then able to infect neighbouring bacteria. Although, bacteriophage were first identified in 1917, studies in the West into their application in medicine have been few and far between but studies have persisted and proved successful in Russia. Even so, various problems with bacteriophage therapy remain. For example, although bacteriophage are easy to grow they are particularly unstable and thus difficult to store.

Bennett et al (1997) describe the immobilisation of a *Salmonella*-specific bacteriophage by adsorption. They detail the passive adsorption of bacteriophage onto polystyrene solid phases. However, this process is inefficient due to complex bacteriophages being immobilised via both "head" and "tail" groups. The tail group is required to be free in order to recognise and infect specific bacteria. Further, the adsorption process is reversible so that adsorbed bacteriophage will desorb and release free bacteriophage. The product of this process is described for use as a separation system for the removal of specific bacteria from foods only and does not require the bacteriophage to be viable.

It is an object of the present invention to obviate and/or mitigate at least some of the above disadvantages.

Broadly speaking, the present invention describes for the first time a method for the immobilisation and optional stabilisation of viruses whilst retaining the viral biological activity. Furthermore, it documents its use in therapy, for example the manufacture of medical devices comprising immobilised virus, such as bacteriophage, with the ability to destroy specific resistant bacteria when, and only when, they are present.

In a first aspect the present invention provides a device comprising virus immobilised to a substrate for medical application.

In a further aspect of the present invention there is provided a device comprising virus immobilised to a substrate for use as an antibiotic (bactericide) or bacteriostatic agent. Preferably, said virus is a bacteriophage.

Immobilisation is understood to relate to a specific physical immobilisaton, such as by chemical bonding and is therefore distinguished from any passive adherence of a virus to a substrate.

The term "virus" according to the present invention includes double-stranded or single-stranded RNA or DNA viruses, which infect cells of bacteria, plants and/or animals. These include viruses from the following families of viruses: Iridoviridae, African swine fever virus, Poxyiridae, Parvoviridae, Reoviridae, Birnaviridae, Picornaviridae, Togaviridae, Flaviviridae, Rhabdoviridae, Bunyaviridae, Herpesviridae, Adenoviridae, Papovaviridae, Hepadnaviridae, Coronaviridae, Calicivirus, Arenaviridae, Paramyxoviridae, Orthomyxoviridae, Filoviridae, Retroviridae, Baculoviridae, Polydnaviridae, Nudaurelia β virus group, Nodaviridae, Caulimovirus, Geminivirus, Tomato spotted wilt virus group, Luteovirus, Machlovirus, Necrovirus, Sobemovirus, Tombusvirus, Tymovirus, Bromovirus, Cucumovirus, Ilarvirus, Alfafa mosaic virus group, Comovirus, Dianthovirus, Nepovirus, Pea enation mosaic virus group, Tobamovirus, Tobravirus, Hordeivirus, Potexvirus, Potyvirus, Carlavirus, Closterovirus, Totiviridae, Partitiviridae, Myoviridae, Styloviridae, Podoviridae, Tectiviridae, Plasmaviridae, Corticoviridae, Microviridae, Inoviridae, Cystoviridae and Leviviridae.

It should be understood that a virus may include viruses or infectious agents, which do not fall into the above mentioned families, e.g., plant satellite viruses, prions, baculoviruses and bacteriophage respectively.

The term "bacteriophage" according to the present invention is indicative of bacteriophage, which infect specific strains of bacteria e.g. *salmonella, Escherichia coli, staphylococcus* or pseudomonus bacteriophage.

The term "medical" according to the present invention is understood to mean the treatment or prevention of viral, bacterial or prion infections and/or contamination in humans, animals or plants. For example, in the case of bacterial infections and/or contamination, treatment or prevention may be achieved by bacteriophage immobilised on a substrate. It will be understood to the skilled man that bacteriophage can recognise and infect specific strains of bacteria. Thus, bacteriophage immobilised to a substrate according to the present invention, may be utilised to fight strain-specific bacterial infections as a "bactericide" by inducing selective killing of bacteria through cell lysis or as a "bacteriostatic agent" by inhibiting bacterial growth. Bacteriophage immobilised to a substrate may also be used as a antibacterial agent/disinfectant in order to "sterilise" bacterially-contaminated material.

The term "substrate" according to the present invention is understood to mean any solid phase material to which a virus may be immobilised. For example, said substrate may be a material which may be advantageously activated to allow head-group specific binding of a virus, such as complex bacteriophage. Said substrate may take many forms, for example, nylon and any other polymer with amino or carboxyl surface groups, cellulose or other hydroxyl-containing polymer, polystyrene or other similar polymer, various plastics or microbeads including magneticparticles, biological substances. More preferably, said substrate is made of a material commonly used in therapy/medicine. For example, nylon thread for use in surgery; plastics, lint or gauze material used to dress open wounds; microbeads, which can be ingested; adhesives such as cyanoacrylates; and/or biological substances such as collagen or hyaluronic acid.

Immobilisation of virus to the substrate may be achieved in a number of ways. Preferably, viruses, such as bacteriophage, are immobilised via bonds, typically covalent bonds formed between the bacteriophage coat protein and the substrate.

More preferably, bacteriophage are immobilised to the substrate via their head groups or nucleocapsid by activating the substrate before the addition and coupling of bacteriophage.

The term "activated/activating/activation" according to the present invention is understood to mean the activation of a substrate by reacting said substrate with various chemical groups (leaving a surface chemistry able to bind viruses, such as bacteriophage head or capsid groups).

Activation of said substrate may be achieved by, for example, preliminary hydrolysis with an acid, preferably HCl followed by a wash step of water and an alkali to remove the acid. Preferably, said alkali is sodium bicarbonate. Binding of viruses, for example bacteriophage, via their head groups is important. In the case of complex bacteriophage for example, binding via head groups leaves the tail groups, which are necessary for bacteria-specific recognition, free to infect, i.e., bind and penetrate a host bacterial cell. It will be understood that this mechanism of infection of a host cell is similar for many other viruses other than viruses that infect and multiply only in bacteria. A plurality of viruses, e.g., various strain-specific bacteriophage, may be immobilised to a substrate at any one time.

Coupling of viruses to a substrate is as a result of the formation of covalent bonds between the viral coat protein and the substrate such as through an amino group on a peptide, for example a peptide bond. "Coupling Agents" that aid this process vary, dependent on the substrate used. For example, for coupling to the substrate nylon or other polymer with amino or carboxy surface groups the coupling agents carbodiimide or glutaraldehyde may be used. For coupling to the substrate cellulose or other hydroxyl-containing polymer the coupling agents vinylsulfonylethylene ether or triazine may be used. Coupling agents for the coupling of virus to the substrate polythene or other similar polymer include corona discharge or permanganate oxidation. Generally speaking, coupling agents for the coupling of bacteriophage to a substrate include: S-Acetylmercaptosuccinic anhydride; S-Acetylthioglycolic acid N-hydroxysuccinimide ester; Adipic acid dihydrazide; 4-Azidobenzoic acid N-hydroxysuccinimide ester; N-(5-Azido-2-nitrobenzyloxy)succinimide ester; 6-(4-Azido-2-nitrophenylamino)hexanoic acid N-hydroxysuccinimide ester; p-Azidophenacyl bromide; 4-Azidosalicylic acid N-hydroxysuccinimide ester; Bromoacetic acid N-hydroxysuccinimide ester; 1,4-Butanediol diglycidyl ether; 2~Diazo-3,3,3-trifluoroproprionic acid p-nitrophenyl ester; Diethyl malonimidate; 4,4'~Diisothiocyanatostilbene-2,2'-disulfonic acid; Dimethyl adipimidate; Dimethyl 3,3'-dithiobispropionimidate; Dimethyl pimelimidate; Dimethyl suberimidate; 4,4'-Dithiobisphenyl azide; Dithiobis(propionic acid N-hydroxysuccinimide ester); Ethylene Glycol bis-(succinic acid N-hydroxysuccinimide ester); 4-Fluoro-3-nitrophenyl azide; p-Formylbenzoic acid N-hydroxysuccinimide ester; Glutaraldehyde; 2-Iminothiolane; 6-(Iodoacetamide) caproic acid N-hydroxysuccinimide ester; Iodoacetic acid N-hydroxysuccinimide ester; 3-Maleimidoacetic acid N-hydroxysuccinimide ester; 3-Maleimidobenzoic acid N-hydroxysuccinimide ester; 4-(N.Maleimido)benzophenone; γ-Maleimidobutyric acid N-hydroxysuccinimide ester; ε-Maleimidocaproic acid N-hydroxysuccinimide ester; 4-(N-Maleimidomethyl)cyclohexenecarboxylic acid N-hydroxysuccinimide ester; 4-(N-Maleimidomethyl) cyclohexanecarboxylic acid 3-sulfo-N-hydroxysuccinimide ester; β-Maleimidopropionic acid N-hydroxysuccinimide ester; N,N'-bis(3-Maleimidopropionyl)-2-hydroxy-1,3-propanediamine; 1,4-Phenylene diisothiocyanete; N,N'-o-Phenylenedimaleimide; Polyoxyethylene bis(glycidyl ether); bis(Polyoxyethylene bis(glycidyl ether);Polyoxyethylene bis(imidazolylcarbonyl)1; Bis (Polyoxyethylene bis[Imidolylcarbonyl]); Polyoxyethylene bis(p-nitropheny) carbonate); 3-(2-Pyridyldithio)propionic acid N-hydroxysuccinimide ester; Suberic acid bis(N-hydroxysuccinimide) ester; Succinic Acid Maleimidoethyl-N-hydroxysuccinimide ester; 1,5-bis(succinimidooxycarbonyloxy)-pentene; bis(N-succinimidyl) carbonate.

Advantageously the present inventor has observed that where virus is immobilised to said substrate, said immobilization confers stability. For example, the immobilised virus is stabilised in such a way that it maintains its viability and infectivity even when in contact with agents, for example proteases, which may otherwise inactivate the virus and similarly, when exposed to physical stress, such as dehydration, temperature or pH which would otherwise inactivate the virus. Further stability is conferred to the immobilised virus using known compounds that protect proteins against dehydration, prolonged storage and other stresses. An example of such a compound is trehalose.

Trehalose and other similar agents including functional analogues are known as stabilizing agents for a number of chemicals, living tissues and even organisms, including viruses (Colaco et al., 1992; Crowe and Crowe 2000). Trehalose, a disaccharide, has been documented to be involved in the stabilisation of membranes and proteins in dry animals and other anhydrobiotic organisms. Such organisms include, for example, dry baker's yeast *Sacchoromyces cerevisiae*, resurrection plants, cysts of certain crustaceans (including the brine shrimp *Artemia*) and many bacteria (Crowe and Crowe, 2000, Nature Biotech., 18, pp 145-146). Trehalose has also been shown to preserve mammalian cells during freezing (Beattie et al., 1997, Diabetes, 46, pp 519-523) and proteins (Colaco et al., 1992, Biotechnology, 10, pp 1007-1011) during drying. Trehalose has also been documented to be involved in the stabilisation of viruses in their native state by Bieganski et al., 1998, Biotechnol. Prog., 14, 615-620. "Stabilization of active recombinant retroviruses in an amorphos dry state with trehalosel".

The present invention not only shows that trehalose may be used to stabilise viruses in their native state but for the first time shows that further stability results from trehalose treatment of viruses immobilised by covalent attachment to a substrate. Thus, in a further aspect of the present invention there is provided use of trehalose for the further stabilisation of a device comprising virus immobilised to a substrate according to the present invention and as hereinbefore described. Covalent immobilization (forming of a chemical bond) of proteins as known, results in a substantial increase in stability. The present inventors have also shown that this is true for bacteriophage by describing herein the stability of an insoluble nylon/bacteriophage co-polymer of considerable molecular weight.

Thus, according to the present invention said virus (es) immobilised to said substrate may be for example, coated with trehalose by, for example, dipping into a solution of trehalose before drying and storage such that the virus(es) maintain their viability and infectivity.

Further applications of the present invention may include the treatment of MRSA; food poisoning, wherein bacteriophage may be immobilised on a substrate such as microbead suspension, which can be ingested; or in the decontamination of hospital equipment/surfaces; Prevention of infection by methicillin-resistant *Staphylococcus aureus* or VISA (vancomycin insensitive *S. aureus*) by immobilization of appropriate bacteriophage onto, for example, sutures or wound dressings; prevention of specific pathogen entry through catheters and similar devices by immobilization of appropriate bacteriophage onto the surface of the device; treatment of pulmonary infection such as tuberculosis with, for example, microparticles of about 10 microns diameter with appropriate bacteriophage immobilized onto them, by inhalation; treatment of infections such as meningitis, for example, by injection of micro particles with appropriate bacteriophage strains immobilized; treatment of gastrointestinal infections, for example, by particles or gels containing appropriate immobilized bacteriophage; treatment of bacterial plant diseases; elimination of, for example, *E. coli* in cattle by incorporation into the diet of immobilized bacteriophage; incorporation of appropriate bacteriophage into food wrapping materials to prevent or eliminate contamination by organisms causing food poisoning; incorporation of appropriate bacteriophage into paints to prevent contamination of surfaces in, for example, hospitals, or farms; treatment of surfaces of air-conditioning units with appropriate immobilized bacteriophage to prevent, for example, *Legionella* contamination.

The present invention may also be used for the purposes of vaccination. For example, the present invention may be used to immobilize any live, infectious virus, which could be then used to vaccinate populations at risk. This may be particularly useful where no vaccine exists for a particular virus and any form of prevention of viral infection would be useful. Thus, a virus as hereinbefore described may be immobilised and used directly to vaccinate reducing the time taken to develop a more standard attenuated virus. It will be understood that such vaccinations may only be conducted, especially with regard to humans, in extreme cases. Without wishing to be bound by theory, the action of the immobilised virus used to vaccinate would be such that the immobilized virus would be unable to reach its target cells from the vaccination site; preventing the immobilised virus infecting the patient. It will be understood, therefore, that immobilised HIV virus would not be able to be used for vaccination in this regard. Preferably, the immobilised virus is kept at the inoculation site for longer than conventional vaccines allowing a better immune response to be raised. Advantageously, the present inventor has shown that the present invention of immobilising viruses substantially reduces or eliminates free, unimmobilised viruses.

In a further aspect, the present invention provides a method of preparing a device comprising a substrate having virus immobilised thereon, said method comprising the steps of:

a) activating the substrate so as to enable virus to bind thereto;
b) mixing the modified substrate with virus and a coupling agent to aid the binding of virus to the substrate.

In a yet further aspect said method comprises the further step of:

c) mixing the device with a stabilising agent that maintains the viability and infectivity of the virus bound to the modified substrate when said modified substrate is exposed to dehydration, prolonged storage and/or other stresses.

It should be understood that the term "activating" is as hereinbefore defined.

Preferably, the stabilising agent according to the present invention is trehalose or other agent such as known heat shock proteins known in the art that protect proteins or viruses against dehydration, prolonged storage and other stresses.

In a preferred embodiment of the present invention, said device mixed with a stabilising agent may be dried, allowing prolonged storage of said device whilst maintaining the infectivity and viability of the virus.

The present invention will now be further described by way of example, with reference to the following methods and figures in which:

FIG. 1—Graphical Representation of Wound Model 1

The graph depicts the activity over three days of nylon strips with or without bacteriophage in killing *Staphylococcus aureus* bacterium present on the surface of raw pork to simulate a surgical wound. The activity represents the average of three replicates, score + or −, wherein + depicts the clearing of bacterium and − depicts the bacterium remaining cloudy.

FIG. 2—Graphical Representation of Wound Model 2

Activity is measure over 9 days and is scored as in FIG. 1. Nylon +/− bacteriophage is inserted into a wound in fresh raw pork, which is replaced with fresh tissue every three days.

FIG. 3—Graphical Representation of Resistance of Immobilised Bacteriophage to Proteolytic Activity Series 1—control;

Series 2—0.1 g/l trypsin;

Series 3—0.5 g/l trypsin;

Series 4—2.5 g/l trypsin

FIG. 4

Graphical representation of numbers of bacteriophage immobilised on activated nylon. The reduction of phage numbers with time is depicted.

FIG. 5

As for FIG. 4, repeated with larger strips of activated nylon (5×1 cm)

FIG. 6

Schematic drawing of Wound Models 1 and 2 (depicted in FIGS. 1 and 2 respectively).

FIG. 7—Graphical Representation of Infection of Animal Cells by Adenovirus.

The graph depicts the infectivity of free adenovirus, and adenovirus immobilised onto nylon on HEK 293 cells.

Methods

Propagation: An overnight subculture of bacteria was adjusted to a cell concentration of $1.5\times10^9$ cells/ml. 0.1 ml of this was mixed with $1\times10^5$ pfu (plaque forming units) of bacteriophage. After incubation at 37° C. for 20 minutes the mixture was poured onto 1.5% LB agar, 0.7% LB agar was layered over this and allowed to set. Plates were incubated at 37° C. for 12 hours. Almost confluent bacteriophage plaques were formed.

Bacteriophage were harvested by adding 5 ml of sterile bacteriophage suspension buffer and shaking. The bacteriophage suspended in the buffer were purified by centrifugation and filtration through a 100 kDa cut-off filter to remove bacterial protein. Yield was $1 \times 10^9$ pfu/ml.

Plaque assays: for the presence of bacteriophage were carried out by the two layer plate assay as described for propagation.

Immobilisation: Nylon strip 8×1 cm was used.

Activation: Nylon was activated by preliminary hydrolysis with 4M HCl for 2.5 minutes at 70° C., washed in distilled water and 0.1M sodium bicarbonate to remove acid.

Coupling to Nylon or Other Polymer with Amino or Carboxyl Surface Groups.

i) Carbodiimide as a Coupling Agent.

After this brief acid hydrolysis of the nylon surface the sample is washed with dimethylformamide (DMF) and 20 mM 1-cyclohexyl-3-[2-morpholinoethyl]-carbodiimidemethyl-p-toluene sulphonate is added. The solution is stirred for 90 minutes, and then the nylon is washed with DMF. The activated nylon is stirred overnight with bacterophage in suitable buffer, and then washed to remove unbound bacteriophage.

ii) Glutaraldehyde as a Coupling Agent.

After a brief acid hydrolysis of the nylon surface the sample is washed with 0.1M bicarbonate buffer pH9.4 and incubated with 10% glutaraldehyde in 0.1M bicarbonate buffer. The surface was then washed in bicarbonate buffer and distilled water before being incubated overnight with bacteriophage in a suitable buffer.

Coupling to Cellulose or Other Hydroxyl-Containing Polymer.

i) Vinylsulfonylethylene Ether

Vinylsulfonyl groups can be introduced into hydroxyl-containing polymers by treatment of the polymer with vinyl sulfone at pH11. The activated polymer is stirred overnight with bacteriophage in suitable buffer, and then washed to remove unbound bacteriophage.

ii) Triazine Addition

Cellulose or a modified cellulose (about log) is added to 50 ml of acetone/water (1:1) containing 1 g 2-amino-4,6-dichloro-s-triazine at 50° and stirred for 5 minutes. Then 20 ml of 15% (w/v) aqueous sodium carbonate to which 0.6 vol. of 1M HCl has been added is poured into the reaction mixture. Concentrated HCl is then added to bring the mixture pH below 7. The amino-chloro-s-triazine substituted cellulose is washed with acetone/water, then water and finally with 0.05M phosphate buffer as pH7.0. The coupling reaction with the bacteriophage is carried out at pH8.0 in 0.05M phosphate buffer by stirring for 12 to 18 hours.

Coupling to Polythene or Other Similar Polymer

1. Corona Discharge

Polythene was exposed to a corona discharge for about 1 second; bacteriophage dehydrated in the presence of trehalose was dusted onto the treated surface immediately.

2. Permanganate Oxidation.

Polythene was exposed to concentrated potassium permanganate solution for several hours, washed with distilled water and immediately treated with bacteriophage in trehalose or other stabilizing agent.

EXAMPLE 1

1. Bacteriophage P1 with *Escherichia coli* 11291

The nylon/bacteriophage preparation was challenged with 50 ml of bacterial culture at about $1 \times 10^8$ cells/ml. After incubation the culture was assayed by the two layer plaque assay.

EXAMPLE 2

Bacteriophage λ Against *E. coli*.

In this experiment the number of pfu's used in the preparation of the immobilised system is compared with the number of pfu's observed when the immobilised system is challenged with the bacteria.

|  | Plaques | | |
| --- | --- | --- | --- |
| Free bacteriophage | 8 | 40 | 35 |
| no bacteriophage | 0 | 0 | 0 |
| Immobilised bacteriophage | 7 | 23 | 17 |

The numbers of bacteriophage plaques arising from the immobilised systems with this bacteriophage-bacteria combination shows:

That immobilised bacteriophage are viable and infective.

a relationship between free bacteriophage numbers used in the preparation and the number of bacteriophage produced by immobilised systems.

EXAMPLE 3

Unknown Bacteriophage Against *Staphylococcus.aureus*

Bacteriophage was isolated by incubating a lawn of *S. aureus* with contaminated water which had been filtered through a 0.18μ filter to remove bacteria. Where a plaque formed indicated the presence of a lytic bacteriophage. This was isolated and grown as previously described.

| Dilution | Plaques expected | Plate count |
| --- | --- | --- |
| 1 | 1 | 0 |
| 2 | 10 | 0 |
| 3 | 100 | 10 |
| 4 | 1000 | 100 |
| 5 | 10000 | 1000 |
| 6 | 100000 | 10000 |

EXAMPLE 4

Effect of Trehalose on Viability

The experimental system was as previously described except that the nylon/bacteriophage preparations were dipped into a trehalose solution of various concentrations and dried before assay (Nylon/bacteriophage preparations previously described were stored in buffer for 24 to 48 hours before use) dried preparations were used 72 hours later.

|  | Plaques |
| --- | --- |
| Free bacteriophage | 24 |
| no bacteriophage | 0 |
| Immobilised bacteriophage | 21 |
| Trehalose 1% | 27 |
| Trehalose 0.5% | 18 |
| Trehalose 0.1% | 24 |
| Trehalose 0.05% | 21 |

The data indicate that trehalose enables immobilised bacteriophage to withstand desiccation and storage for at least 72 hours without significant loss of viability and infectivity. The free bacteriophage, no bacteriophage and immobilised bacteriophage samples were controls not treated to desiccation and storage.

| Dilution | Plaques expected | Plate count |
| --- | --- | --- |
| 1 | 1 | 1 |
| 2 | 10 | 1 |
| 3 | 100 | 15 |
| 4 | 1000 | 250 |
| 5 | 10000 | 500 |
| 6 | 100000 | 1000 |

The data show that significant numbers of viable and infective bacteriophage have been immobilised on the nylon sheet. There is also a dose/response relationship between the estimated numbers of bacteriophage immobilised and the plaques formed from the immobilised system.

Validation of Washings:

The washings from the nylon/bacteriophage reaction were assayed by the two layer plaque assay to determine the rate and efficiency of removal of free bacteriophage (those that did not form covalent attachment as a result of the chemistry).

| Washing | pfu/ml |
| --- | --- |
| 1 | 10000 |
| 2 | 100 |
| 3 | 8 |
| 4 | 0 |
| 5 | 0 |
| 6 | 0 |

EXAMPLE 5

Bacteriophage NCIMB 9563 (ATCC6538-B) Against *Staphylococcus aureus* in the Presence of Tissue Bacteriophage 9563 was grown as previously described, immobilized onto nylon membrane, washed to remove unbound bacteriophage and tested against a strain of *S. aureus* in two experimental situations.

1. Does the presence of animal tissue affect the response of the immobilised bacteriophage?

The nylon membrane with immobilized bacteriophage was placed in a flask with 50 ml of *S. aureus* growth medium and 10 g of macerated beef, to model a wound situation, the flask was inoculated with $2 \times 10^8$ bacterial cells and incubated for 24 hours at 37° C. Samples were tested for the presence of bacteriophage by the two layered assay previously described. The results showed that the macerated tissue did not significantly affect the infection of *S. aureus* by immobilized bacteriophage 9536.

| Dilution | Plaques expected | Plate count |
| --- | --- | --- |
| 1 | 1 | 0 |
| 2 | 10 | 0 |
| 3 | 100 | 10 |
| 4 | 1000 | 100 |
| 5 | 10000 | 1000 |
| 6 | 100000 | 10000 |

The "plaques expected" is based on the estimated number of bacteriophage immobilized and their expected subsequent propagation in the bacterial culture. The result implies that under the conditions of the experiment about 10% of the immobilized bacteriophage infected bacteria or, more likely, that 10% of the inoculated bacteria came into contact with the nylon membrane.

2. Does the immobilized bacteriophage have an effect in a wound model?

A series of two-centimeter cuts were made in a beef or pork slice and each was inoculated with $2 \times 10^8$ bacterial cells. Sections of nylon membrane with immobilized bacteriophage 9536 were inserted into ten of the cuts, nylon membrane without bacteriophage into another ten, and ten left untreated.

After 24 hours visible growth was evident in cuts left untreated or treated with nylon only, but no growth was seen in cuts treated with immobilized bacteriophage. This indicates that immobilized bacteriophage is effective in preventing bacterial growth in the presence of muscle tissue.

EXAMPLE 6

1. Wound Models:

In a hypothetical clinical situation where sutures with immobilised bacteriophage had been used, the longer the phage remained active the greater the protection given. Although the major period of contamination would be during and immediately after surgery, the material would not be activated until contact between target bacteria and the suture occurred.

Figure 6A:

Initial experiments used surface contact with fresh, raw pork to simulate a surgical wound—See FIG. 6*a*.

The assay involved incubating the exposed nylon/phage strips with the target *S. aureus* (8588) cultures. Exposed strips were sterilized with chloroform (2.5%) to prevent contamination from other bacteria present on the pork surface. The target bacterium was either cleared (+result) or remained cloudy (−result).

Conclusions:

Activity is substantially retained for three days in contact with "wound"—see FIG. 1.

Wound Model 2

Figure 6B:
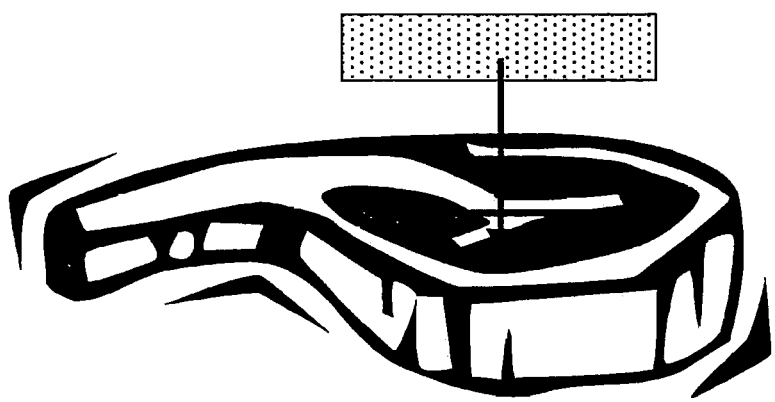
Figure 7:
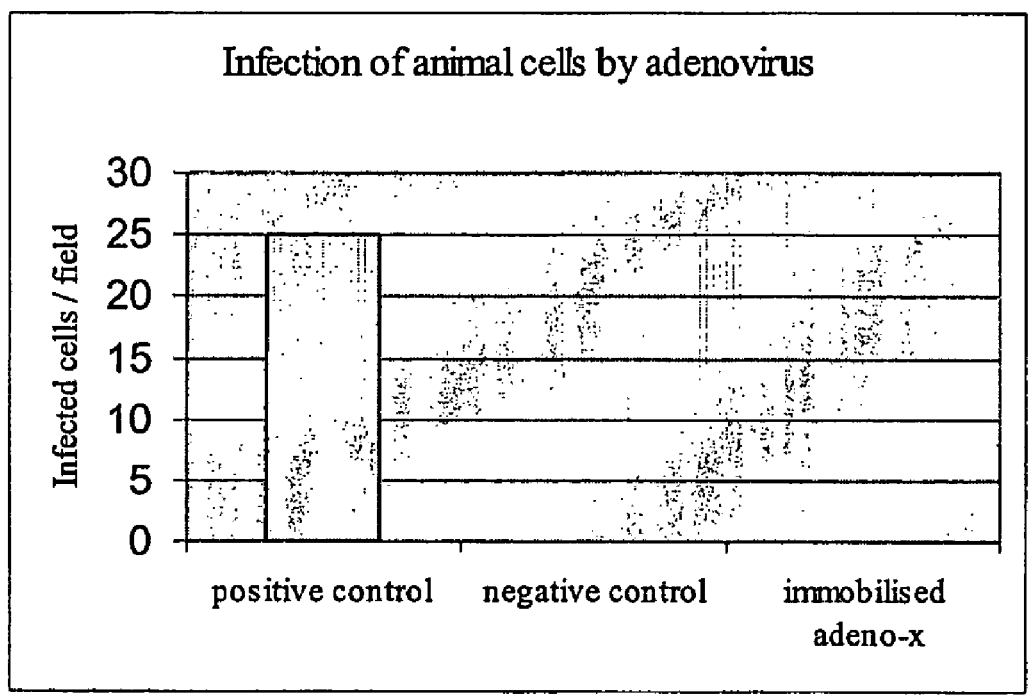

In this test, the strips (nylon/phage) were inserted into a wound in fresh raw pork, which was replaced with fresh tissue every three days—see FIG. 6*b*.

Figure 2:
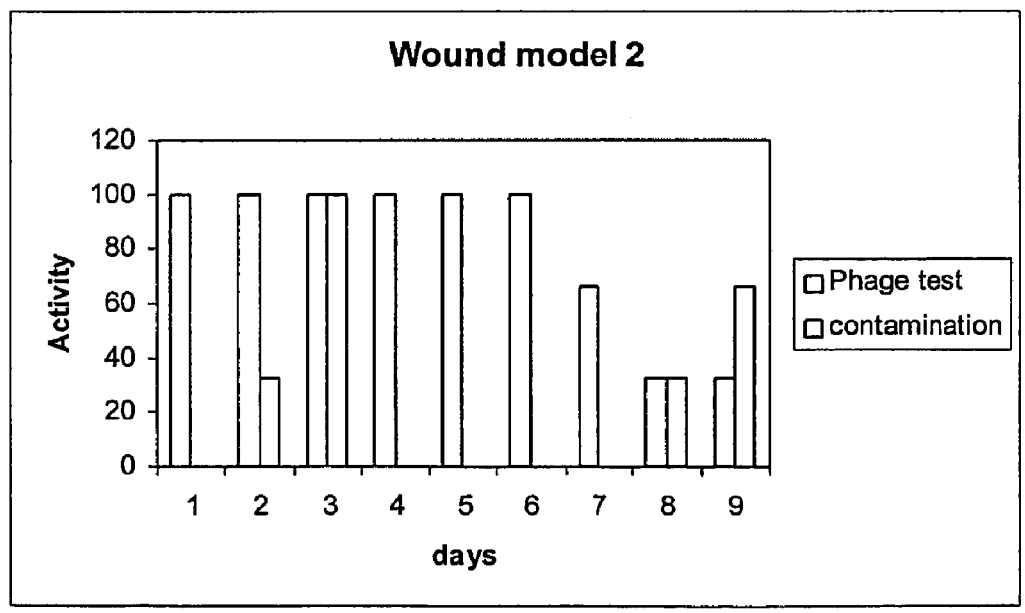

Results are depicted in FIG. 2

Conclusions:

The activity was retained at a high level for 6 to 7 days. After that period, one or more of the replicate strips failed to clear the *S. aureus* culture. This result suggests that a single presentation would provide protection for longer than the likely time sutures would be used, and longer than the time in which wound dressings would be left unchanged.

Trypsin Digest

The aim of this was to determined how resistant phage were to proteolytic degradation, a possible stress in certain situations. Two experimental approaches were used, free bacteriophage were tested to determine their susceptibility to tryptic inactivation and immobilised bacteriophage were tested, to determine any protective effect from the immobilization.

Free phage test 1.

Three concentrations of trypsin were used:

0.1 g/l 0.5 g/l 2.5 g/l

Tests were carried out in universal tubes with 5 ml of stock phage.

Samples were diluted and assayed for viable phage by standard plaque assay.

Figure 3:
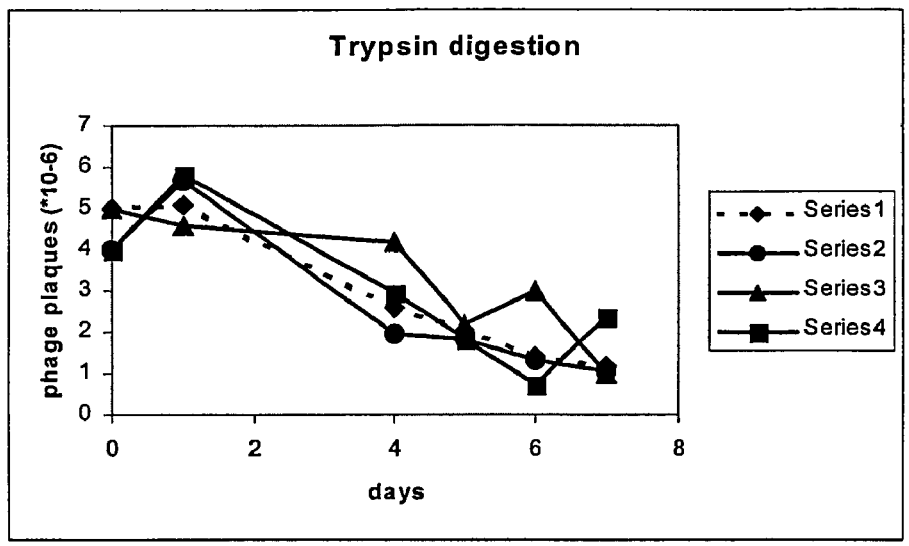
Figure 4:
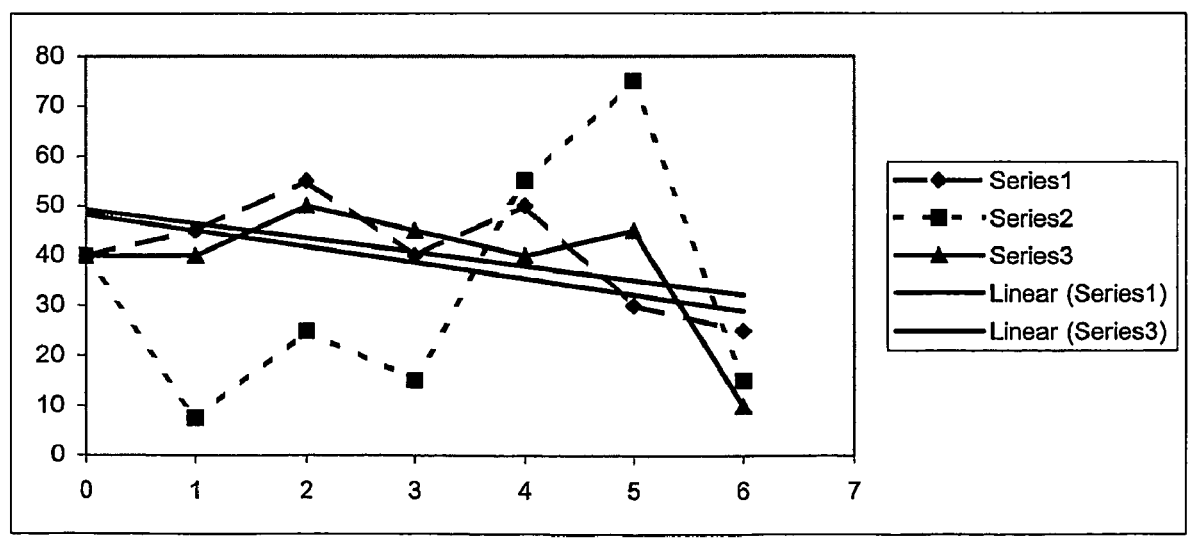

Results are depicted in FIG. 3

Conclusions:

The trypsin at these concentrations and times was without effect on the free phage.

This experiment was repeated three times with similar outcomes.

The immobilised phage is at least as resistant as the free phage to proteolytic inactivation.

This result has implications for possible oral administration of bacteriophage.

Numbers of Phage Immobilised

Two approaches have been adopted, one is to determine the residual phage after immobilization and the other electron microscopy.

1. Activated nylon was added to phage solution of known concentration and the reduction of phage numbers with time measured by plaque assay.

Figure 5:
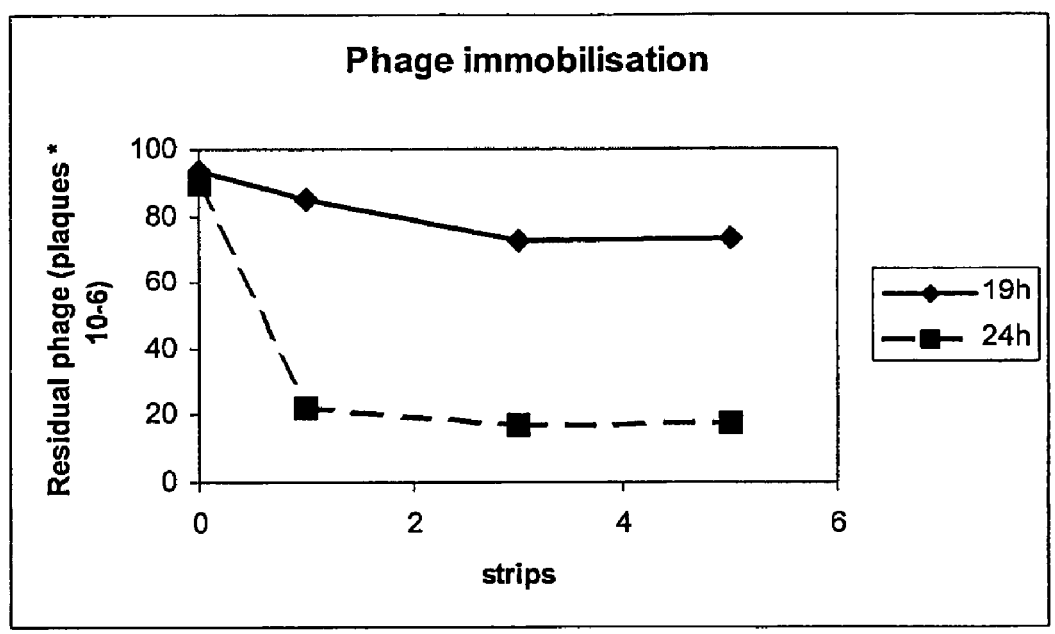

Results are depicted in FIG. 5

The area of the strips was 5×1 cm, with the number of phage immobilised being $7 \times 10^7$ per strip. This gives a density of one phage per $15\mu^2$, electron microscopy methods give a similar density (7 to 15μ spacing). The size of phage is about 0.3μ, so the surface density could be increased.

EXAMPLE 7

Production of Lytic Bacteriophage Active Against Pathological Strains of S. aureus.

Method

A lytic bacteriophage isolated from environmental sources was treated with mutagenic chemicals to alter the binding capability of the bacteriophage towards its target bacterium. Random mutagenesis can be carried out by any standard method, in the case reported below this was treatment with hydroxylamine (4%).

| Antibiogram | Methicillin MIC | Phage type | PFGE profile | Plaques with mutant |
|---|---|---|---|---|
| PuSuTe(MtCxErCp) | R | 932/77ih/ 83A/84IH/ 85/90+ | PF108a | None |
| PnMtCx | R | 75w | PF15a | Confluent |
| PnMtCxErCp(Im) | R | NT | PF15b | Confluent |
| PnMtCxErClCpKmTb | R | 83Cw/29ih/ 75w/77w/ 83Aw | PF16a | Confluent |
| PnMtCxImErClCpKm | R | 83Cih/29ih/ 52ih/75w/ 77/83Aw | PF16m | Confluent |

Conclusions

PF15a and b correspond to EMRSA type 15, which accounts for about 70% of hospital-acquired infections. PF16a and M correspond to EMRSA type 16 which accounts for about 20% of such infections. This phage would be effective against 90% of all hospital-acquired infections in the UK.

EXAMPLE 8

Activity of Immobilised Adenovirus Background.

Method

Nylon samples were activated with carbodiimide as previously indicated and reacted with Adeno-X-LacZ™ viral stock (BD Biosciences Palo Alta, USA). The samples were washed 5 times, then introduced into wells of a 12 well assay plate. Healthy HEK 293 cells ($5 \times 10^5$ cells/ml) were seeded into each well, together with positive and negative controls. The positive control consisted of un-immobilised Adeno-X_LacZ virus ("free virus"). Cells were cultured in DMEM+ 10% Fetal Bovine serum medium. Several dilutions of the stock virus were used ($10^{-2}$ to $10^{-6}$). Plates were incubated at 37° C. in 5% $CO_2$/air for 48 hours. The medium was removed cells air dried for 5 minutes, then fixed by adding 1 ml ice-cold methanol to each well. After 10 minutes the methanol was removed and wells rinsed three times with 1 ml Phosphate buffered saline (PBS)+1% bovine serum albumin (BSA).

Anti-hexon antibody (BD Biosciences Palo Alta, USA) was diluted 1:1000, and 0.5 ml added to each well, incubated for 1 hour at 37° C. with shaking.

The antibody was removed, wells rinsed three times with PBS+1% BSA. Rat Anti-Mouse antibody (Horse radish peroxidase conjugate), diluted 1:500, was added to each well (0.5 ml), incubated with shanking for a further 1 hour at 37° C., then rinsed three times with PBS=1% BSA (1 ml). DAB working solution was prepared by dilution of the 10× concentrate with Stable peroxidase buffer (BD Biosciences Palo Alta, USA).

0.5 ml of DAB working solution was added to each well and incubated at room temperature for 10 minutes. The DAB solution was removed and 1 ml PBS added.

Immunisation Protocol

The Adeno-X-LacZ™ viruses were immobilised onto nylon spheres of approximately 10 microns diameter, using the carbodiimide protocol previously described and washed five times. About 0.25 ml of a suspension of the nylon spheres with immobilised adenovirus in complete Freunds Adjuvant were injected into Balb C mice, and a further 0.3 ml injected after three weeks.

Mice were bled 14 days after the final injection and the serum tested for the presence of antibody to the adenovirus.

Adeno-X-LacZ™ immobilised onto nylon was treated with diluted serum from the mice instead of the Anti-hexon antibody, otherwise the protocol was as described in the previous section.

Sampling

Wells with cell layers were viewed using an inverted microscope under 10, 20 and 40× objectives with bright field and phase contrast.

Nylon squares were mounted on slides and viewed with bright field and phase contrast microscopy under 10, 20 and 40× objectives.

Darkly brown-stained cells were interpreted as infected (+). Unstained cells as uninfected (−)

Results

The immobilised adenovirus was incapable of infecting the HEK 293 cells, although the free virus was infective. This indicates that immobilization prevents phagocytosis of virus particles by animal cells, and hence infection by the virus.

The immobilised adenovirus, when injected into rats, gave an immune response indicating that the adenovirus protein was present on the surface of the nylon.

REFERENCES

Bennett, A. R., Davids, FGC., Vlahodimou, S., Banks, J. G. and Betts, R. P., 1997. Journal of Applied Microbiology, 83, 259-265.

Colaco, C., Sen, S., Thangavelu, M., Pinder, S., and Roser, B., 1992. Biotechnology, 10, 1007-1011.

Crowe, J. H., and Crowe, L. M., 2000. Nature Biotechnology, 18, 145.

The invention claimed is:

1. A device for use in the prevention and/or treatment of a bacterial infection and/or contamination comprising bacteriophage immobilised to a substrate wherein the immobilised bacteriophage is immobilised to the substrate via covalent bonds formed between the bacteriophage head group or nucleocapsid and the substrate, such that the bacteriophage retains infectivity.

2. A device according to claim 1 for use as an antibiotic (bactericide) or bacteriostatic agent.

3. A device according to claim 1 wherein immobilisation confers increased stability to said bacteriophage.

4. A device according to claim 1 wherein said device has a plurality of different strain-specific bacteriophage immobilised thereon.

5. A device according to claim 1 wherein said substrate is a material which is activated to allow head-group specific binding of a bacteriophage.

6. A device according to claim 1 wherein said bacteriophage is immobilised via its head group leaving the tail group free.

7. A device according to claim 1 wherein said immobilisation of bacteriophage to a substrate via a covalent bond is aided by the addition of a coupling agent.

8. A device according to claim 7 wherein said coupling agent is carbodiimide or glutaraldehyde for coupling of bacteriophage to the substrate nylon or other polymer with amino or carboxy surface groups; vinylsulfonylethylene ether or triazine for coupling [of bacteriophage] to the substrate cellulose or other hydroxyl-containing polymer; permanganate oxidation for the coupling of bacteriophage to the substrate polythene or other similar polymer.

9. A device according to claim 5 wherein the activation is carried out by corona discharge.

10. A device according to claim 1 wherein said immobilised bacteriophage is treated with a compound that protects proteins against dehydration, prolonged storage and other stresses and wherein said immobilised bacteriophage displays increased viability and an infectivity when treated in comparison to untreated bacteriophage.

11. A device according to claim 10 wherein said compound is trehalose.

12. A medical device for prevention and/or treatment of a bacterial infection and/or contamination, the device comprising bacteriophage immobilised to a substrate, wherein the bacteriophage is immobilised to the substrate via covalent bonds formed between the bacteriophage head group or nucleocapsid such that the bacteriophage retains infectivity.

13. The device according to claim 12 in the form of a bandage, suture, compress or wound-dressing, implant, bead, plaster, or the like.

14. A device comprising bacteriophage immobilised to a substrate wherein the substrate has been activated using corona discharge and the bacteriophage is immobilised to the substrate via covalent bonds formed between the bacteriophage head group or nucleocapsid such that the bacteriophage retains infectivity.

15. The device according to claim 14 for prevention and/or treatment of a bacterial infection and/or contamination.

* * * * *